(12) United States Patent
Derungs (10) Patent No.: US 10,175,935 B2
(45) Date of Patent: Jan. 8, 2019

(54) METHOD OF VIRTUAL REALITY SYSTEM AND IMPLEMENTING SUCH METHOD

(71) Applicant: Louis Derungs, Chigny (CH)

(72) Inventor: Louis Derungs, Chigny (CH)

(73) Assignee: E-PNOgraphic Sàrl (CH)

( * ) Notice: Subject to any disclaimer, the term of this patent is extended or adjusted under 35 U.S.C. 154(b) by 7 days.

(21) Appl. No.: 15/347,544

(22) Filed: Nov. 9, 2016

(65) Prior Publication Data

US 2018/0046432 A1 Feb. 15, 2018

(30) Foreign Application Priority Data

Aug. 10, 2016 (CH) .................................. 1031/16

(51) Int. Cl.
*G06F 17/00* (2006.01)
*G06F 3/16* (2006.01)
(Continued)

(52) U.S. Cl.
CPC .............. *G06F 3/165* (2013.01); *A61B 5/02* (2013.01); *A61M 21/02* (2013.01); *G02B 27/0172* (2013.01); *A61M 21/0094* (2013.01); *A61M 2021/005* (2013.01); *A61M 2021/0011* (2013.01); *A61M 2021/0027* (2013.01); *A61M 2205/507* (2013.01); *A61M 2230/04* (2013.01); *A61M 2230/63* (2013.01); *G02B 2027/014* (2013.01); *G02B 2027/0141* (2013.01); *G02B 2027/0178* (2013.01)

(58) Field of Classification Search
CPC .............................. A61B 5/02; G02B 27/0172; G02B 2027/014; G02B 2027/0141; G02B 2027/0178; G06F 3/165; A61M 21/02; A61M 21/0094; A61M 2021/0011; A61M 2021/0027; A61M 2021/005; A61M 2205/507; A61M 2230/04; A61M 2230/63
USPC ................................ 700/94; 348/14.01–14.16
See application file for complete search history.

(56) References Cited

U.S. PATENT DOCUMENTS 7,537,576 B1 * 5/2009 Worley, III ............ A61H 1/001
  601/46
8,517,912 B2   8/2013 Clare
(Continued)

FOREIGN PATENT DOCUMENTS

WO   WO 2013/049248 A2   4/2013

*Primary Examiner* — Hemant S Patel
(74) *Attorney, Agent, or Firm* — Blank Rome LLP (57) ABSTRACT

Virtual reality method intended to be implemented in a virtual reality system, the method including the production of a stimulus in the system during a period of stimulation, the stimulus including: a projection of an image sequence; a production of a first sound signal including a soundtrack linked to the progress of the image sequence; a production of a second sound signal having a first frequency and a third sound signal having a second frequency, the second sound signal being audible from one ear and the third sound signal being audible from the other ear of the user; a production of a fourth sound signal including a spoken presentation; during an initial portion of said predetermined period, the stimulus further including an induction signal; and during a final portion of said predetermined period, the intensity of the sound signals decreasing in intensity until a zero intensity, and the image sequence decreasing in intensity until a zero intensity.

29 Claims, 5 Drawing Sheets

(51) Int. Cl.
    *A61B 5/02*     (2006.01)
    *G02B 27/01*     (2006.01)
    *A61M 21/02*     (2006.01)
    *A61M 21/00*     (2006.01)

(56) References Cited

U.S. PATENT DOCUMENTS

| | | | |
|---|---|---|---|
| 9,325,938 B2* | 4/2016 | Paragano | H04N 7/141 |
| 2006/0247489 A1 | 11/2006 | Carbis et al. | |
| 2006/0252979 A1 | 11/2006 | Vesely et al. | |
| 2010/0010289 A1* | 1/2010 | Clare | A61M 21/00 600/27 |
| 2011/0301727 A1* | 12/2011 | Ansfield | G04G 13/02 700/94 |
| 2013/0170650 A1 | 7/2013 | Fujisawa et al. | |
| 2013/0301845 A1* | 11/2013 | Royal | G10K 11/175 381/71.6 |
| 2014/0067130 A1* | 3/2014 | Pillai | H04L 12/2816 700/275 |
| 2014/0171729 A1* | 6/2014 | Bourne | A61M 21/00 600/27 |
| 2014/0316191 A1 | 10/2014 | de Zambotti et al. | |
| 2014/0350706 A1* | 11/2014 | Morishima | G10K 15/04 700/94 |
| 2015/0174362 A1 | 6/2015 | Panova et al. | |

\* cited by examiner

METHOD OF VIRTUAL REALITY SYSTEM AND IMPLEMENTING SUCH METHOD

TECHNICAL FIELD

The present invention relates to a virtual reality method and a system implementing such a method.

PRIOR ART

The use is known of a device for supporting a user or a patient so as to lead them into a deep altered state of consciousness until a deep state of hypnosis.

Document U.S. Pat. No. 8,517,912 describes a medical hypnosis device for controlling a hypnosis experience in a patient. The device includes output means for providing a first type of content that may be a virtual reality type of representation.

Document US2006247489 describes a device and a method of relaxation and meditation by hypnosis in a virtual environment. The device includes an audiovisual headset connectable to a portable DVD player for playing movies from DVD media so as to lead the user into a state of relaxation until a deep state of hypnosis. The device may include a 2D or 3D monitor.

Document US2015174362 describes an apparatus including a virtual reality module and a method for inducing a state of hypnosis. The apparatus includes a head-mounted display for delivering a virtual reality audiovisual signal to the patient and collecting their biological signals.

BRIEF SUMMARY OF THE INVENTION

The present invention relates to a virtual reality method intended to be implemented in a virtual reality system, the method including the production of a stimulus in the system during a period of stimulation, the stimulus including:

a projection of an image sequence;

a production of a first sound signal including a soundtrack linked to the progress of the image sequence;

a production of a second sound signal having a first frequency and a third sound signal having a second frequency, the second sound signal being audible from one ear and the third sound signal being audible from the other ear of the user;

a production of a fourth sound signal including a spoken presentation;

during an initial portion of said predetermined period, the stimulus further including an induction signal; and during a final portion of said predetermined period, the intensity of the sound signals decreasing in intensity until a zero intensity, and the image sequence decreasing in intensity until a zero intensity.

The present invention also relates to a virtual reality system adapted to the virtual reality method and to a computer medium including portions of code of an application program intended to be executed by the virtual reality system so as to implement the method.

These solutions notably offer the advantage compared with the prior art of providing more effective relaxation and meditation techniques compared with the prior art.

BRIEF DESCRIPTION OF THE FIGURES

Examples of implementation of the invention are set out in the description illustrated by the appended figures in which.

EXAMPLE(S) OF EMBODIMENT

Figure 1:
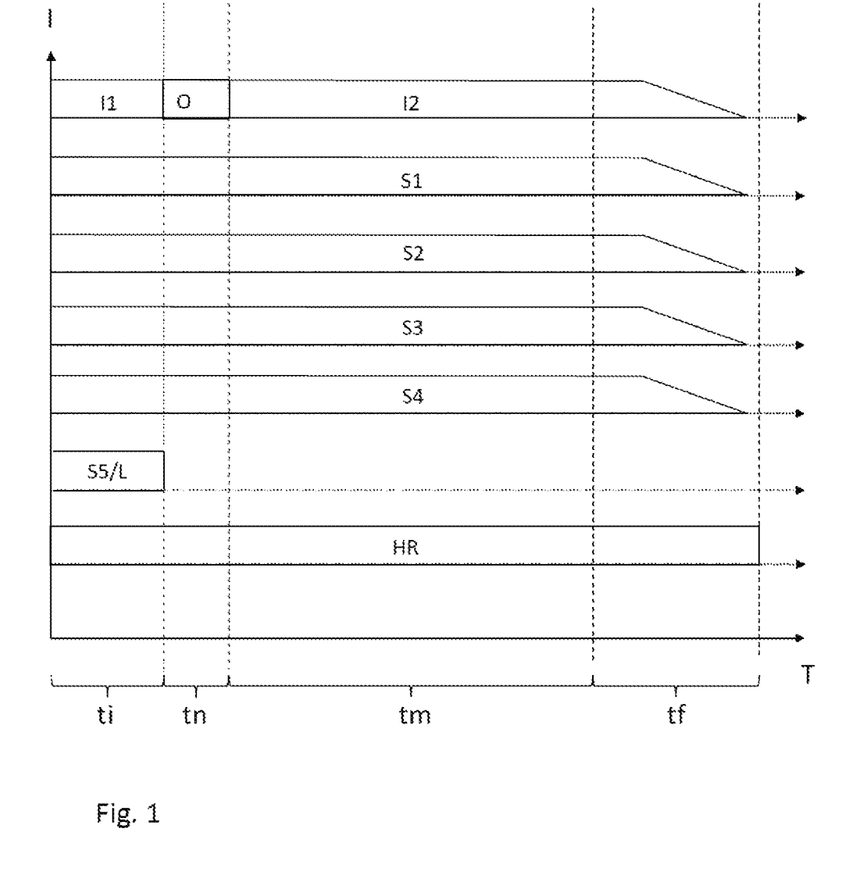
FIG. 1 schematically illustrates a virtual reality system including a virtual reality device and a display device, according to one embodiment.

FIG. 1 represents a virtual reality method intended to be implemented in a virtual reality system, according to one embodiment. The method includes the production of a stimulus during a period of stimulation. The stimulus may include a projection of an image sequence I1. The stimulus may also include the production of the first sound signal S1 including a soundtrack linked to the progress of the image sequence I1. The stimulus may also include the production of the second sound signal S2 having the first frequency f1 and of the third sound signal S3 having the second frequency f2. The second sound signal is audible from one ear of a the user and the third sound signal being audible from the other ear of the user. The stimulus may also include the production of a fourth sound signal S4 including a spoken presentation.

During an initial portion ti of the period of stimulation, the stimulus further includes an induction signal S5. During a final portion tf of the period of stimulation, the intensity of the sound signals S1-S4 decrease in intensity until a zero intensity, and the image sequence I1 decreasing in intensity until a zero intensity.

According to one implementation, the first frequency f1 of the second sound signal S2 differs from the second frequency f2 of the third sound signal S3. For example, the difference between the first and the second frequency f1, f2 may be constant over one portion or the whole of the period of stimulation. In particular, the difference between the first and the second frequency f1, f2 is between 5 Hz and 12 Hz.

According to one implementation, the first and the second frequency f1, f2 vary during the portion or the whole of the stimulation period, so that the difference between the first and the second frequency f1, f2 remains constant. Typically, the first and the second frequencies f1, f2 are between 20 Hz and 600 Hz.

In one embodiment, the fourth sound signal S4 includes a spoken presentation forming a discourse of a hypnotic character. The fourth sound signal S4 may be pre-recorded or recited by an operator through a device in communication with the virtual reality system 1. The spoken presentation may be used to influence and lead the user 10 toward a state of relaxation and mediation.

Figure 2:
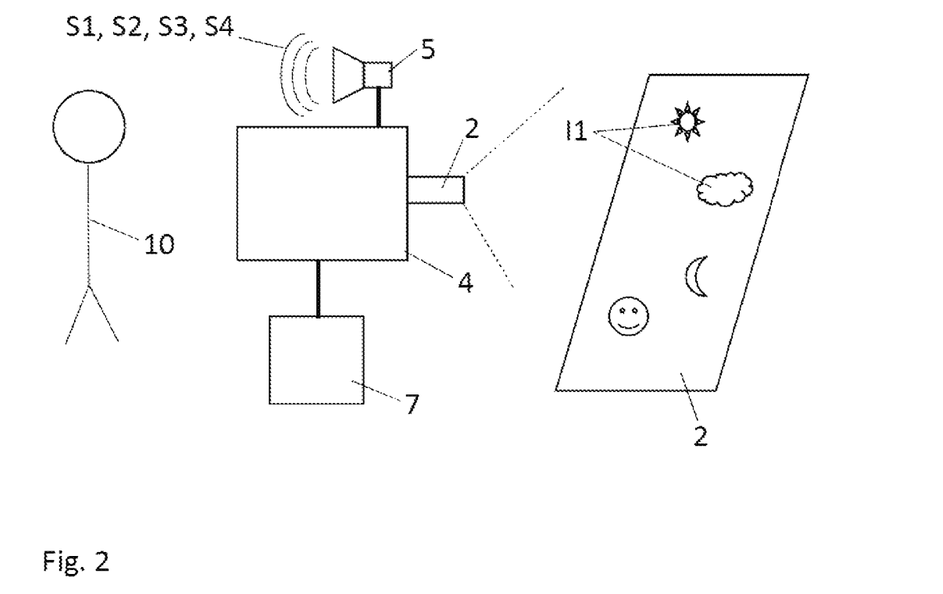
FIG. 2 represents a method intended to be implemented in the virtual reality system, according to one embodiment.

FIG. 2 schematically illustrates a virtual reality system 1 adapted to the implementation of the method, according to one embodiment. The system 1 includes a virtual reality module 4 comprising a display device 2 configured for projecting an image sequence I1 in the visual field of a user 10. The virtual reality module 4 also includes an audio playback device 5 configured for producing the first sound signal S1, the second sound signal S2 having the first frequency f1 and audible from one ear of the user, the third sound signal S3 having the second frequency f2 and audible from the other ear of the user, and the fourth sound signal S4 including a spoken presentation. The system 1 also includes a control unit 7 configured for controlling the virtual reality module 4. The projection of the image sequence I1 with the soundtrack S1 by means of the display device 2 and the audio playback device 5 of the virtual reality system 1 may be used to simulate the presence of the user 10 in the real or imaginary environment projected by the image sequence I1 (e.g. a movie). The virtual reality system 1 may allow a playback of movies with sound or image sequences with sound and customized, notably at the request of the user 10.

The virtual reality system 1 may be adapted so that the second sound signal S2 and the third sound signal S3 are respectively only audible by one or the other ear of the user 10.

The projection of the image sequence I1 implemented by the virtual reality system 1 allows the user to interact spatially with the projected environment, e.g. by changing the angle of view of the environment by changing their posture, e.g. by turning their head or torso.

Figure 3:
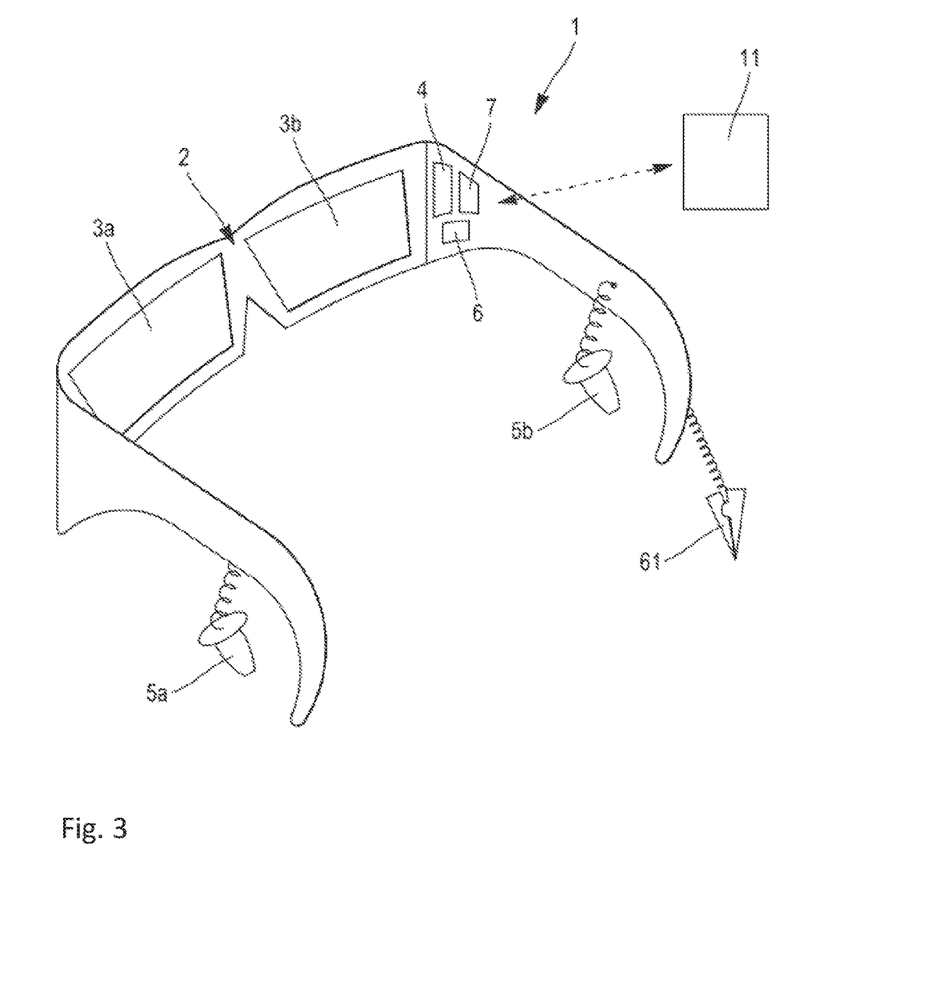
FIG. 3 depicts the virtual reality system according to a particular embodiment.

FIG. 3 depicts the virtual reality system 1 according to a particular embodiment in which the system 1 takes the form of eyeglasses 1 worn by the user. The display device 2 includes two display screens 3*a*, 3*b* corresponding to the lenses of the eyeglasses so that each display screen 3*a*, 3*b* is in the visual field of one of the two eyes of the user 10, when the system 1 is worn by the latter.

According to one implementation, the audio playback device 5 includes two transducers 5*a*, 5*b*, e.g. in the form of earpieces. Each transducer 5*a*, 5*b* allows the production of the second sound signal S2 and the third sound signal S3 in each of the ears of the user 10.

In one embodiment, during a median portion tm subsequent to the initial portion ti and preceding the final portion tf, the production of the image sequence I1 allows an interaction of the user with the image sequence I1. For example, characteristics of the image sequence I1, notably the light intensity, are changed by the interaction of the user 10.

The median portion tm may therefore allow the user to interact with the image sequence I1 and/or with the fourth sound signal S4.

For example, the image sequence I1 may include one or a plurality of virtual objects that appear and/or disappear as a result of the interaction of the user 10. The interaction of the user 10 may include includes a movement of the user in relation to the object. Alternatively, the movement of the user 10 may include directing the gaze of their eyes and/or an orientation of their head (e.g. in the direction of an object or objects) for a predetermined period of time.

The display device 2 may be arranged so that the image sequence I1 produced allows an interaction of the user 10. For this purpose, the display device 2 may be configured for changing the characteristics of the image sequence I1, e.g. the light intensity of the images, as a result of an interaction of the user 10.

Advantageously, the display device 2 is configured so as to cause one or a plurality of virtual objects included in the image sequence I1 to appear and/or disappear, as a result of an interaction of the user 10. The appearance and/or the disappearance of the virtual object or objects may occur in a predefined period of time after the interaction, so as to induce a beneficial state of mind in the user.

The user 10 may be led, by means of the spoken presentation S4, to indicate one or more virtual objects with which they interact. The spoken presentation S4 may also be used to identify the virtual object or objects with which the user 10 will interact. The interaction may also be performed orally by the user 10 only or in addition to the movement of the user 10.

Figure 4:
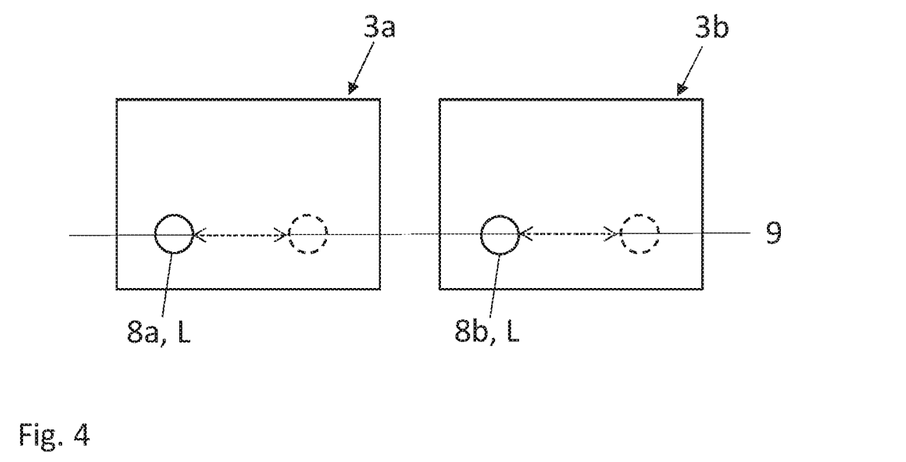
FIG. 4 depicts a display device, according to one embodiment.

According to one implementation, during the initial portion ti of the period of stimulation, the induction signal S5 includes a projection of a light signal L superimposed on the image sequence I1 (see FIG. 4). The light signal L may be displaced in a random or predetermined movement between a first and a second area of the image sequence I1. In a variant, the light signal L is displaced rhythmically in a to-and-fro movement between a first and a second area of the image sequence I1. The purpose of the induction signal S5 is to facilitate the transition of the user to a state of relaxation and meditation, or even hypnosis.

During the initial period ti, the projection of the image sequence I1 with the soundtrack S1 may take on a scenic character, favoring relaxation in the user 10. The image sequence I1 may thus allow the user 10 to view a succession of backgrounds. In addition, one or more light patterns (such as a dot or other) may be superimposed on the image sequence. Each light pattern may have a distinct and uniform color. These images, possibly with the light pattern or patterns, may be used, for example, to implement a calm and relaxing scene and/or chromotherapy techniques.

At the end of the initial period ti, the production of the induction signal S5 ceases.

FIG. 4 illustrates the display device 2 configured for simultaneously displaying a first virtual object 8*a* (or a light signal L) via the first display screen 3*a* and a second virtual object 8*b* (or another light signal L) via a second display 3*b*. Such an arrangement may be used to generate a stereoscopic vision effect, i.e. to reproduce a perception of a relief of the virtual object 8*a*, 8*b* from two plane images illustrated by the two screens 3*a*, 3*b*. These virtual objects may be superimposed on the image sequence I1.

The first virtual object 8*a* may be displaced rhythmically in a to-and-fro movement between a first and a second area of the first screen 3*a*. In a similar way, the second virtual object 8*b* may be displaced rhythmically in a to-and-fro movement between a first and a second area of the second screen 3*b*.

In the example in FIG. 4, the first virtual object 8*a* and the second virtual object 8*b* are displaced along a line of displacement 9 virtually linking the first screen 3*a* and the second screen 3*b* so as to displace the objects 8*a*, 8*b* between a right peripheral portion and a left peripheral portion of the field of vision of each eye. Such a configuration may be used, for example, to implement EMDR type implementation protocols developed by Shapiro.

Advantageously the display device 2 may be configured for dynamically varying the angle of the line of displacement 9 (with respect to the geometric arrangement of the screens 3*a*, 3*b*) in response to the lateral inclination of the system 1, when it is worn by the user 10. The line of displacement 9 may thus be maintained substantially parallel to the horizontal (i.e. perpendicular to the direction of gravity).

According to another implementation, the induction signal includes a production of a fifth sound signal S5. The fifth sound signal S5 may be displaced in a random or predetermined movement. In a variant, the fifth sound signal S5 is displaced in a to-and-fro movement between a first and a second area in the space surrounding the user.

According to one implementation, the audio playback device 5 may be configured in such a way that the induction signal S5 includes a two-channel sound being rhythmically displaced in a to-and-fro movement between a first and a second area of the space surrounding the user 10. In a preferred manner, the virtual sound source S5 may be displaced along a line virtually connecting the first and the second transducer 5a, 5b (see FIG. 3). This last configuration may be used to implement EMDR type implementation protocols developed by Shapiro.

In particular, the virtual reality system 1 is adapted to implementing a virtual reality method that requires the user 10 to perform a sequence of eye movements, this in combination with sound signals and/or predetermined image sequences which may produce scenes or other visual environments.

In one embodiment, the period of stimulation includes a dark portion tn subsequent to the initial portion ti and preceding the median portion tm, in which the image sequence consists of a total darkness O. During the dark period tn, the image sequence O simulates an environment of total darkness, e.g. by a series of dark images or by a reduction in the intensity of the images until a zero intensity or one perceived as zero. The dark period tn may be used to strengthen and verify the state of relaxation and meditation in the user 10.

In yet another embodiment, the virtual reality system 1 includes at least one sensor module 6 configured for measuring a vital parameter HR (biofeedback) of the user 10. For example, the sensor module 6 may include a sensor for providing a cardiovascular signal, that may be used, for example, to determine the cardiac coherence of the user 10. Such a sensor may include an optical device such as a photoplethysmographic sensor or an ECG or ICG (impedance cardiography) sensor. FIG. 3 illustrates a photoplethysmographic sensor module taking the form of an ear-clip 61.

The control unit 7 may be configured for controlling the sensor 6 and possibly collecting and analyzing the cardiovascular signal provided by the sensor 6, e.g. so as to determine a cardiac coherence as well as a cardiac coherence threshold.

According to one implementation, the method includes a step of determining the cardiac coherence of the user 10 with the aid of the cardiovascular signal provided by the sensor module 6, during the median portion tm. The method may further include a step of returning to the initial portion ti of the period of stimulation in which the induction signal S5 is generated in order to put the user back into the desired state (e.g. in the event of a state of relaxation that is insufficient or lacking), when the determined cardiac coherence is below the cardiac coherence threshold. The initial period ti may be extended or repeated so as to induce a sufficient state of relaxation and meditation of the user.

The control unit 7 may include a transmission module (not represented) arranged for allowing data collected by the control unit 7 to be transmitted to an external module 11. The external module 11 may be configured for processing and/or displaying and/or storing the collected data. The external module 11 may also be arranged for receiving commands and/or images or image sequences intended to be generated by the display device 2 and/or to receive commands and/or sounds intended to be generated the audio playback device 5.

Advantageously, the control unit 7 may be configured for receiving voice messages from a third party so as to play them back through the audio playback device 5.

In particular, the control unit 7 may be configured for generating a database of image sequences and accessing the database so as to allow the user to download the new visual content in order to be played back with the system 1.

Figure 6:
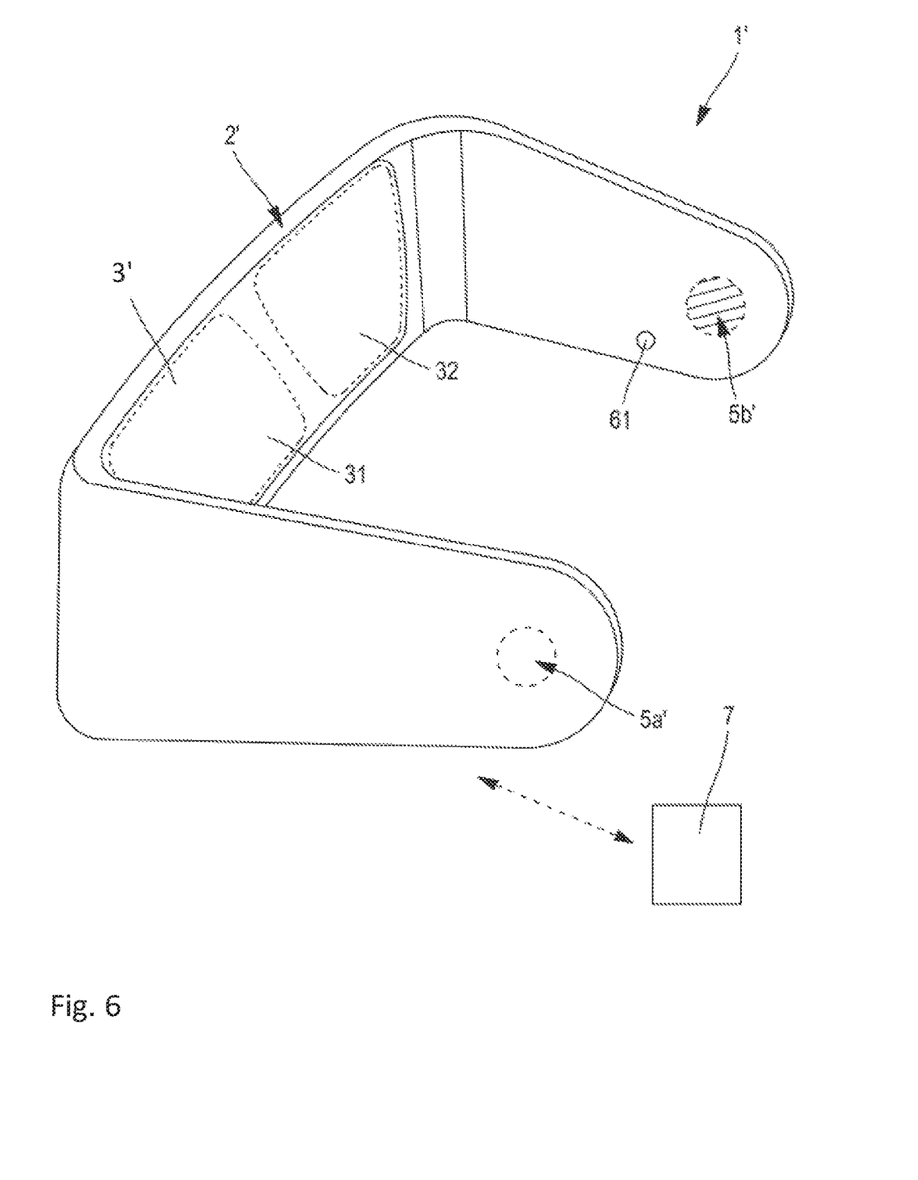
FIG. 6 depicts a variant embodiment of the virtual reality system.

FIG. 6 illustrates a variant embodiment of the virtual reality system 1. Here, the portable system 1 takes the form of a helmet-mounted display (sometimes also called a head-mounted display, immersive headset, virtual reality helmet, helmet-display or HMD helmet). This variant of the system 1 takes on the technical characteristics of the system 1 in FIG. 3. However, the display device 2 includes a single display screen 3 covering the fields of vision of both eyes of the user. A first portion 31 of the display screen 3 is positioned in the visual field of the first eye of the user, and a second portion 32 of the screen is positioned in the visual field of the second eye of the user, when the latter is wearing the system 1.

The virtual reality module 4 may be configured for displaying the first virtual object 8a and/or the second virtual object 8b via the same display screen 3. Advantageously, the virtual reality module 4 is configured for displaying the first virtual object 8a being displaced in the first portion 31 of the screen 3 and simultaneously the second object 8b being displaced in the second portion 32 of the screen 3 so as to generate a stereoscopic vision effect.

In particular, the virtual reality module 4 may be configured for displaying the first virtual object 8a being displaced rhythmically in a to-and-fro movement between a first and a second area of the first portion 31 of screen 3. The virtual reality module 4 may also be configured for displaying the second virtual object 8b being displaced rhythmically in a to-and-fro movement between a first and a second area of the second portion 32 of screen 3.

The display device 2 is arranged so that each portion of the screen 3a, 3b, 31, 32 is positioned only in one of the two fields of vision of the eyes of the user.

Figure 5:
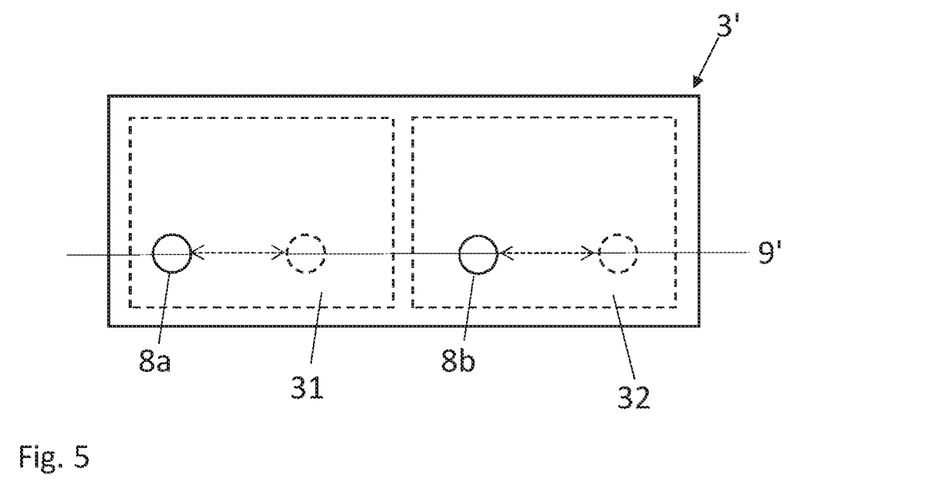
FIG. 5 illustrates an example of a display device, according to another embodiment.

FIG. 5 illustrates an example in which the display device 2 is configured so that the first virtual object 8a and the second virtual object 8b are displaced along a line of displacement 9 virtually linking the two lateral edges of the display screen 3. The virtual reality module may thus be used to implement EMDR type implementation protocols developed by Shapiro.

Advantageously the virtual reality module may be configured for dynamically varying the angle of the line of displacement 9 (with respect to the lateral edges of the display screen 3) in response to the lateral inclination of the system 1, when it is worn by the user 10. The line of displacement 9 may thus be maintained substantially parallel to the horizontal (i.e. perpendicular to the direction of gravity).

The system 1 according to the variant in FIG. 6 allows an integration of the first and second transducer 5a, 5b of the stereophonic audio playback device. The transducers 5a, 5b may thus take the form of speakers. The system 1 allows an easy integration of the sensor module 6.

According to an implementation illustrated in FIGS. 1 and 6, the control unit 7 is remote from the display device 2. The whole or a part of the virtual reality module 4 may also be remote from the display device 2. The control unit 7 (possibly also the whole or a part of the virtual reality module 4) and the sensor module 6 communicate with one another with the aid of a wireless communication protocol. In a variant, the control unit 7 and possibly also the whole or a part of the virtual reality module 4 are included in a portable apparatus such as a smartphone, a tablet, etc.

The method may include an initial step of collecting information via the virtual reality system 1. This information may be collected through a virtual questionnaire so as to allow a calibration of the various steps of the method (intensity of the sound signals S1-S5 and images I1) as well as the setting of its periods (ti, tn, tm, tf). The virtual reality system 1 may include vocal means, such as a microphone, or optical means (camera) or any other appropriate means for collecting information.

The method may be adapted to sports preparation, increasing the physical performance of an athlete, personal development, relaxation, mediation, desensitization to smoking or unhealthy eating habits, as well as preparation for dental and orthopedic operations of short duration, replacing general convenience anesthesias and installing a virtual gastric ring.

In particular, the method may be adapted to hypnosis, e.g. a combination of hypnosis and an EMDR (Eye Movement Desensitization and Reprocessing) and/or EFT (Emotional Freedom Technique) type technique.

The present invention also relates to a computer medium including portions of code of an application program intended to be executed by the control unit 7 so as to implement the method described here.

REFERENCE NUMBERS USED IN THE FIGURES

1 virtual reality system
2 display device
3 display screen
3a first screen
3b second screen
31 first portion of the display screen
32 second portion of the display screen
4 virtual reality module
5 audio playback device
5a first transducer
5b second transducer
6 sensor module
61 clip
7 control unit
8a first virtual object
8b second virtual object
9 line of displacement
10 user
11 external module
I1 image sequence
f1 first frequency
f2 second frequency
HR vital parameter
L light signal
O total darkness
S1 first sound signal
S2 second sound signal
S3 third sound signal
S4 fourth sound signal
S5 induction signal
tf final portion
ti initial portion
tm median portion
tn dark portion

The invention claimed is:

1. Virtual reality method intended to be implemented in a virtual reality system, the method including the production of a stimulus in the system during a period of stimulation, wherein the period of stimulation comprises an initial portion, a median portion subsequent to the initial portion and preceding a final portion, the stimulus including, during the initial, median and final portions:

a projection of an image sequence;
a production of a first sound signal including a soundtrack linked to the progress of the image sequence;
a production of a second sound signal having a first frequency and a third sound signal having a second frequency, the second sound signal being audible from one ear and the third sound signal being audible from the other ear of the user; and
a production of a fourth sound signal including a spoken presentation;
during the initial portion of said period of stimulation, the stimulus further including an induction signal; and
during the final portion of said period of stimulation, the intensity of the sound signals decreasing in intensity until a zero intensity, and the image sequence decreasing in intensity until a zero intensity.

2. Method according to claim 1,
said spoken presentation being a discourse of a hypnotic character.

3. Method according to claim 1,
in which, during a median portion subsequent to the initial portion and preceding the final portion, the production of the image sequence allows an interaction of the user with the image sequence.

4. Method according to claim 3,
in which characteristics of the image sequence, notably the light intensity, are changed by the interaction of the user.

5. Method according to claim 3,
in which the image sequence includes one or a plurality of objects that appear and/or disappear as a result of an input of the user.

6. Method according to claim 5,
in which the user's input includes a movement of the user in relation to the object.

7. Method according to claim 6,
in which the movement of the user includes directing the gaze of their eyes and/or an orientation of their head for a predetermined period of time.

8. Method according to claim 1,
in which the first frequency differs from the second frequency; and
in which the difference between the first and the second frequency is constant over the whole of the period of stimulation.

9. Method according to claim 8,
in which the difference between the first and the second frequency is between 5 Hz and 12 Hz.

10. Method according to claim 8,
in which the first and the second frequency are between 20 Hz and 600 Hz.

11. Method according to claim 8,
in which the first and the second frequency vary during the portion or the whole of the period of stimulation, so that the difference between the first and the second frequency remains constant.

12. Method according to claim 1,
in which the induction signal includes a projection of a light signal superimposed on the image sequence.

13. Method according to claim 12,
in which the light signal is displaced in a random or predetermined movement between a first and a second area of the image sequence.

14. Method according to claim 12,
in which the light signal is displaced rhythmically in a to-and-fro movement between a first and a second area of the image sequence.

15. Method according to claim 1,
in which the induction signal includes a production of a fifth sound signal.

16. Method according to claim 15,
in which the fifth sound signal is displaced according to a random or predetermined movement.

17. Method according to claim 15,
in which the fifth sound signal is displaced in a to-and-fro movement between a first and a second area in the space surrounding the user.

18. Method according to claim 1,
in which, during a predetermined portion subsequent to the initial portion and preceding the median portion, the image sequence consists of a total darkness.

19. Method according to claim 1,
in which the virtual reality device includes at least one sensor configured for measuring a vital parameter of the user; and
including the determination and follow-up of the vital parameter during at least one portion of the predetermined period.

20. Method according to claim 19,
in which the vital parameter of the user includes a cardiac coherence parameter.

21. Method according to claim 20,
including the determination of a cardiac coherence threshold; and
returning to the initial portion in which the induction signal is generated, when the determined cardiac coherence is below the cardiac coherence threshold.

22. Method according to claim 20,
used in the virtual reality system for one of the following applications or a combination of these methods: sports preparation, increasing the physical performance of an athlete, personal development, relaxation, mediation, desensitization to smoking or unhealthy eating habits, preparation for dental and orthopedic operations of short duration, replacing general convenience anesthesias and installing a virtual gastric ring, hypnosis, combination of hypnosis and an Eye Movement Desensitization and Reprocessing (EMDR) type of technique.

23. Virtual reality system, including:
a virtual reality device comprising a virtual reality module configured for producing a stimulus during a period of stimulation, wherein the period of stimulation comprises an initial portion, a median portion subsequent to the initial portion and preceding a final portion, the virtual reality device further comprising a display device configured for projecting an image sequence in the visual field of a user during the initial, median and final portions; an audio playback device configured for producing a first sound signal including a soundtrack, a second sound signal having a first frequency and audible from one ear of the user, a third sound signal having a second frequency and audible from the other ear of the user, a fourth sound signal including a spoken presentation, wherein the first, second, third and fourth sound signals being produced during the initial, median and final portions; and an induction signal produced during the initial portions; and
a control unit configured for controlling the virtual reality module.

24. System according to claim 23,
in which the virtual reality module is configured for projecting a virtual object being displaced between a first and a second area of a display surface of said display device.

25. System according to claim 23,
said virtual reality module being configured for generating a two-channel sound simulating a virtual sound source being displaced rhythmically in a to-and-fro movement between a first and a second area of space surrounding the user.

26. System according to claim 23,
including a sensor module for sensing a vital parameter of the user.

27. System according to claim 26,
in which the sensor module includes a sensor for providing a cardiovascular signal; the control unit being adapted so as to be able to determine the cardiac coherence of the user from the cardiovascular signal.

28. System according to claim 23,
being portable, preferably the control unit and/or the whole or a part of the virtual reality module being remote from the display device.

29. A non-transitory computer medium including portions of code of an application program intended to be executed by the control unit so as to implement the method according to claim 1.

* * * * *